(12) United States Patent
Jiao et al.

(10) Patent No.: US 10,837,035 B2
(45) Date of Patent: Nov. 17, 2020

(54) METHOD FOR EXTRACTING CITRULLINE FROM WATERMELON

(71) Applicant: ZHENGZHOU FRUIT RESEARCH INSTITUTE CHINESE ACADEMY OF AGRICULTURAL SCIENCES, Zhangzhou (CN)

(72) Inventors: Zhonggao Jiao, Zhengzhou (CN); Jiechao Liu, Zhengzhou (CN); Chunling Zhang, Zhengzhou (CN); Qiang Zhang, Zhengzhou (CN); Hui Liu, Zhengzhou (CN); Zhenzhen Lv, Zhengzhou (CN); Wenbo Yang, Zhengzhou (CN); Dalei Chen, Zhengzhou (CN)

(73) Assignee: ZHENGZHOU FRUIT RESEARCH INSTITUTE CHINESE ACADEMY OF AGRICULTURAL SCIENCES, Zhengzhou (CN)

( * ) Notice: Subject to any disclaimer, the term of this patent is extended or adjusted under 35 U.S.C. 154(b) by 0 days.

(21) Appl. No.: 16/888,779

(22) Filed: May 31, 2020

(65) Prior Publication Data
US 2020/0291437 A1 Sep. 17, 2020

Related U.S. Application Data

(63) Continuation of application No. PCT/CN2019/076459, filed on Feb. 28, 2019.

(51) Int. Cl.
| | | |
|---|---|---|
| *C12P 13/10* | (2006.01) | |
| *C07C 273/18* | (2006.01) | |
| *B01D 9/00* | (2006.01) | |
| *B01D 11/02* | (2006.01) | |
| *B01D 15/36* | (2006.01) | |

(52) U.S. Cl.
CPC ............... *C12P 13/10* (2013.01); *B01D 9/00* (2013.01); *B01D 11/0265* (2013.01); *B01D 11/0288* (2013.01); *B01D 15/361* (2013.01); *C07C 273/189* (2013.01)

(58) Field of Classification Search
CPC ............................ C12P 13/10; C07C 273/189
See application file for complete search history.

(56) References Cited

U.S. PATENT DOCUMENTS 8,173,837 B1 * 5/2012 Fish .................... C07C 273/189
562/514
9,173,837 B2 11/2015 Hillis et al.

FOREIGN PATENT DOCUMENTS

| CN | 101372465 A | 2/2009 |
|---|---|---|
| CN | 101880245 A | 11/2010 |
| CN | 103360283 A | 10/2013 |
| CN | 105400851 A | 3/2016 |

OTHER PUBLICATIONS

First Office Action dated May 27, 2019 issued in Chinese Application No. 201811002367.1.

* cited by examiner

*Primary Examiner* — Robert J Yamasaki
*Assistant Examiner* — Charles Zoltan Constantine
(74) *Attorney, Agent, or Firm* — SZDC Law P.C.

(57) ABSTRACT

The present invention relates to the technical field of natural substance extraction. Disclosed is a method for extracting Citrulline from a watermelon. The method for extracting Citrulline from a watermelon in the present invention comprises Raw material pretreatment, ultrasound-enzymatic hydrolysis assisted solvent leaching, and purification steps. The purification step comprises microbial fermentation, ion-exchange resin purification, macroporous adsorption resin discoloration, and crystallization and recrystallization. The method for extracting Citrulline in the present invention is simple, requires a mild condition, and has a good extraction effect on Citrulline. The purity of Citrulline after purification is more than 90%. In addition, the Citrulline extracted by the method in the present invention meets the related health requirements and product quality standards, can be applied to food and health food industries as a raw material, and has natural security advantages.

7 Claims, 2 Drawing Sheets

METHOD FOR EXTRACTING CITRULLINE FROM WATERMELON

This application is Bypass Continuation Application PCT/CN2019/076459, filed on Feb. 28, 2019, which claims priority to Chinese Patent Application No. 201811002367.1, filed on Aug. 30, 2018, all of which are incorporated by reference for all purposes as if fully set forth herein.

BACKGROUND OF THE INVENTION

1. Technical Field

The invention belongs to the technical field of natural substance extraction, and particularly relates to a method for extracting Citrulline from watermelon.

2. Description of Related Art

Watermelons are widely planted in China, with short growth cycles and high yields. The annual planting area is about 2 million hectares, with a total output of 68 million tons, accounting for 58.99% and 71.45% of the world's total watermelon cultivation area and total output respectively, and both ranking first in the world. Due to the strong seasonality of watermelon planting, the market is concentrated, and it is not easy to store. The imbalance between supply and demand has caused watermelon prices to fall sharply or even to overstock, causing a lot of decay. In addition, the defective melons in the planting process are not suitable for fresh sales, and often can only be rotten in the ground or sold extremely cheaply, resulting in a waste of resources. The key to solving these problems lies in vigorously developing deep processing of watermelon and increasing the added value of watermelon.

At present, domestic watermelon processing usually focuses on the development of watermelon beverages (including watermelon juice, watermelon wine, watermelon vinegar, etc.) and watermelon sauce. However, the quality of watermelon (for example, the degree of maturity and freshness) is expected highly during processing into primary products for direct consumption. Even so, the watermelon will lose its original flavor after heat treatment, and it is still difficult to meet the taste of consumers. Therefore, the operability of processing watermelon into beverages or jams is poor and difficult to achieve industrialization.

Citrulline, also known as Carbamylornithine ornithin, is named after it was first isolated from watermelon juice. It has the functions of improving the immune system, maintaining joint movement and the balance of blood glucose levels, scavenging free radicals, keeping normal cholesterol levels, improving healthy sexual function, leading to smooth muscle relaxation, relaxing blood vessels, maintaining healthy lung function, improving mental clarity, reducing stress, overcoming depressed mood, and many other physiological effects.

At present, the extraction method of Citrulline in watermelon is generally including water extraction, membrane filtration, cation exchange resin adsorption, decolorization of activated carbon or macroporous resin, and crystallization and recrystallization. For example, the method disclosed in the patent 200810056075 includes juice extraction, ultrafiltration and nanofiltration, ion-exchange resin adsorption, decolorization, and spray drying. Patent 200610113510 and 200710120714 disclosed the main steps of method, including membrane treatment, ion-exchange resin adsorption, and crystallization. Patent 200510072130 disclosed a method using juice concentration, ion-exchange resin adsorption, and crystallization. Zhou Xiaohua et al. published a method of "Separating L-Citrulline from Trichosanthes kirilowii Maxim by HD-8 Resin". The method disclosed was the use of trichosanthin as a raw material for water extraction, ion-exchange resin adsorption, and macroporous resin adsorption and decolorization.

The above processes have poor impurity removal effects, high energy consumption, and low product content. In addition, the Citrulline crude extract contains sugar, protein, starch and other substances in addition to Citrulline, which seriously affects the further isolation and purification of Citrulline. Therefore, the extraction solution needs to be pretreated to ensure the effect of further purification. The sugar content in the crude extract will affect the viscosity of the crude extract, making it difficult to cross the column, and it will also affect the crystallization.

BRIEF SUMMARY OF THE INVENTION

In view of the problems existing in the prior art, the object of the present invention is to provide a method for the extraction and purification of Citrulline in watermelon, which can not only efficiently extract the Citrulline from watermelon, but also keep the high purity of Citrulline. Indicators of the extracted Citrulline such as heavy metals and microorganisms meet relevant sanitary requirements and product quality standards.

The technical solution adopted by the invention to fulfill the above objective is as follows:

A purification method of Citrulline, the steps are as follows:

(1) Microbial fermentation: add yeast to the liquid of Citrulline crude extract to ferment for 24 hours;

(2) Ion-exchange resin purification: the liquid of Citrulline extract after microbial fermentation was filtered to remove yeast and added to the activated wet resin to adsorb Citrulline, and then eluted with 0.5 mol/L ammonia solution to obtain Citrulline eluent; the elution rate is 2 BV/h;

(3) Macroporous adsorption resin discoloration: mix activated wet resin with Citrulline eluent at 1:20 (g/mL), and perform static adsorption on condition of 100-150 r/min at room temperature;

(4) Crystallization and recrystallization:

a. The crude Citrulline extract is concentrated under vacuum to a soluble solid with the content ≥30%; The pH of the concentrated solution is adjusted to 5.97, and the Citrulline crystals are precipitated at 4° C.; The precipitate is centrifuged, washed, and dried to obtain Citrulline crystals with white powdered solid;

b. Dissolve the Citrulline powder of step (a) with water, adjust the pH to 5.97, add 0.1% Citrulline crystals as seeds crystals, precipitate the Citrulline crystals at 4° C., and centrifuge to separate the precipitates;

c. Repeat step (b) 1-2 times, centrifuge the precipitate, wash, and dry to obtain a refined Citrulline solid powder.

In one embodiment, the added amount of the yeast is 5% (v/v).

The ion-exchange resin purification mentioned include shaker static adsorption or dynamic exchange adsorption.

The shaker static adsorption is that the activated wet resin is mixed with the Citrulline extract solution after fermentation by the microorganism according to 1:15-20 (g/mL), and keeping the condition of 100-150 r/min for 15 min to achieve the static adsorption.

The dynamic exchange adsorption is that 180 g of activated wet resin is packed in a glass chromatography column with an inner diameter of 26 mm and a height of 400 mm, and the Citrulline extract solution after fermentation by microorganisms is passed through the resin column at a speed of 2-6 BV/h to adsorb Citrulline.

The ion-exchange resin is one of D001, D113, HD-8, 732 and 252H; And the macroporous adsorption resin is one of XDA-5, XAD-761, AB-8, and HZ-803.

A method for extracting Citrulline from watermelon, comprising the steps of raw material pretreatment, ultrasound-enzymatic hydrolysis assisted solvent leaching and purification.

The step of purification is:

(1) Microbial fermentation: 5% (v/v) yeast is added to the Citrulline extract or mixed solution of the Citrulline extract and melon peel juice to ferment for 24 hours to remove sugar;

(2) Ion-exchange resin purification: the Citrulline extract after microbial fermentation is filtered to remove yeasts, and added to HD-8 activated wet resin to adsorb Citrulline, and then eluted with 0.5 mol/L ammonia solution for 2 BV/h of the elution rate to obtain Citrulline;

(3) Macroporous adsorption resin discoloration: mix XAD-761 activated wet resin with Citrulline eluent at 1:20 (g/mL), and perform static adsorption on condition of 100-150 r/min for 2 hours at room temperature to obtain crude Citrulline extract;

(4) Crystallization and recrystallization:

a. The crude Citrulline extract is concentrated under vacuum to a soluble solid with the content ≥30%, the pH of the concentrated solution is adjusted to 5.97, and the Citrulline crystals are precipitated at 4° C.; The precipitate is centrifuged, washed, and dried to obtain a white powdered solid of Citrulline crystals;

b. Dissolve the Citrulline powder of step (a) with water, adjust the pH to 5.97, add 0.1% Citrulline crystals as seed crystals, precipitate the Citrulline crystals at 4° C., and centrifuge to separate the precipitates;

c. Repeat step (b) 1-2 times, centrifuge the precipitate, wash, and dry to obtain a refined solid powder of Citrulline.

The enzymolysis is that adding 0.1-0.2% (m/m) biological enzyme to the pretreated material with the temperature maintaining at 40-50° C., and then performing 1-2 hours of enzymolysis;

The biological enzyme is one or two of pectinase and cellulase.

Wherein the step of ultrasound-enzymatic hydrolysis assisted solvent leaching, the extraction conditions are: material-liquid ratio 1:10-1:20 (kg/L), ultrasound power 100-140 W, extraction temperature 30-50° C., extraction time 60-120 min, and extraction times twice.

The method for extracting Citrulline from watermelon includes the following steps:

Raw Material Pretreatment

After the outer skin of the watermelon rind is removed, the rind is squeezed and filtered to obtain filter residue or the rind which is dried is ground into a powder;

Ultrasound-Enzymatic Hydrolysis Assisted Solvent Leaching

Water is added to the pretreated material at a material-liquid ratio of 1:10-1:20 (kg/L), and then 0.1% (m/m) of pectinase and 0.1% (m/m) of cellulose are also added to the above pretreated material; Adjust pH to 4.0, ultrasonic power to 100-140 W, extraction temperature to 30-50° C., extraction time to 60-120 min, and extraction times twice to obtain an extract;

Purification (1) Microbial fermentation: 5% (v/v) yeast is added to the extract or mixed solution of the extract and melon peel juice to ferment for 24 hours to remove sugar;

(2) Ion-exchange resin purification: the liquid of Citrulline extract after microbial fermentation is filtered to remove yeasts, and added to HD-8 activated wet resin to adsorb Citrulline, and then eluted with 0.5 mol/L ammonia solution to obtain Citrulline eluent; the elution rate is 2 BV/h;

(3) Macroporous adsorption resin discoloration: mix XAD-761 activated wet resin with Citrulline eluent at 1:20 (g/mL), and perform static adsorption on condition of 100-150 r/min for 2 hours at room temperature;

(4) Crystallization and recrystallization.

a. The crude Citrulline extract is concentrated under vacuum to a soluble solid with the content ≥30%, the pH of the concentrated solution is adjusted to 5.97, and the Citrulline crystals are precipitated at 4° C.; The precipitate is centrifuged, washed, and dried to obtain a white powdered solid of Citrulline crystals;

b. Dissolve the Citrulline powder of step (a) with water, adjust the pH to 5.97, add 0.1% Citrulline crystals as seed crystals, precipitate the Citrulline crystals at 4° C., and centrifuge to separate the precipitates;

c. Repeat step (b) 1-2 times, centrifuge the precipitate, wash, and dry to obtain a refined solid powder of Citrulline.

The Citrulline which be prepared by the above method.

The Citrulline is used in the preparation of foods for enhancing immunity, anti-oxidation, improving exercise function, protecting cardiovascular and cerebrovascular, and improving male sexual function.

Preferably, the food is a health product.

The strain number of yeast is CICC-1012, China Center of Industrial Culture Collection.

The pectinase and cellulase were purchased from Tianjin Lihua Enzyme Preparation Technology Co., Ltd., and the enzyme activity is 1000 U/mg.

Advantages of the Technical Solution of the Present Invention

The present invention uses watermelon rind as a raw material, and extracts Citrulline using an enzymatic hydrolysis treatment and an ultrasound-assisted solvent extraction. The extraction conditions are mild and the extraction rate of Citrulline is as high as 93.43%. In addition, the method of microbial degradation is used to remove the sugar from the crude extract. The above conditions are mild, the operation is simple and safe, and it has almost no effect on the content of Citrulline. The purity of Citrulline obtained by ion exchange resin purification, macroporous adsorption resin decolorization and recrystallization purification is high. The resin has a long service life, is easy to be regenerated, and has a low cost. The Citrulline extracted by the present invention can be used as a raw material in the food and health care products industry, and has natural advantages of safety.

The physicochemical and hygienic indicators of the Citrulline extract obtained by the present invention are tested, and the quality standards of it is compared with commercially available Citrulline products. The results show that the Citrulline obtained by the present invention meets the relevant health requirements and quality standard.

DETAILED DESCRIPTION OF THE INVENTION

Figure 1:
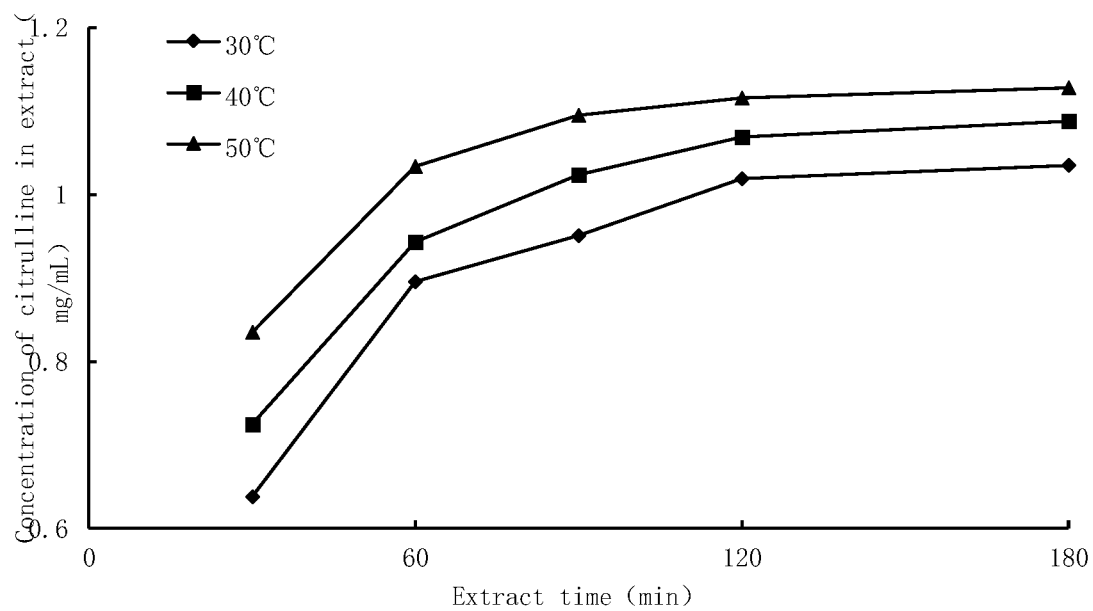
FIG. 1 shows the effect of temperature and time on Citrulline extraction.

Terms used in the present invention have the meanings generally understood by those of ordinary skill in the art unless otherwise specified.

The present invention will be described in further detail with reference to specific embodiments and with reference to data. The following examples are only for the purpose of illustrating the present invention, and are not intended to limit the scope of the present invention in any way.

Embodiment 1

A method for extracting Citrulline from watermelon, the steps are as follows:

1. Raw Material Pretreatment

After the outer skin of the watermelon rind is removed, the rind is squeezed and filtered to obtain filter residue or the rind which is dried is ground into a powder;

2. Ultrasound-Enzymatic Hydrolysis Assisted Solvent Leaching

Water was added to the pretreated material at a material-liquid ratio of 1:10 (kg/L), and then 0.1% (m/m) of pectinase and 0.1% (m/m) of cellulose were also added to the above pretreated material. Adjusted the pH of the enzymatic hydrolysis to 4.0, ultrasonic power to 100 W, extraction temperature to 50° C., extraction time to 90 min, and extraction times twice to obtain an extract.

3. Purification (1) Microbial fermentation: 5% (v/v) yeast was added to the extract or mixed solution of the extract and melon peel juice to ferment for 24 hours to remove sugar.

(2) Ion-exchange resin purification: the liquid of Citrulline extract after microbial fermentation was filtered to remove yeasts, and added to HD-8 activated wet resin to perform the dynamic exchange adsorption of Citrulline, and then eluted with 0.5 mol/L ammonia solution to obtain Citrulline eluent; the elution rate is 2 BV/h;

The dynamic exchange adsorption is that 180 g of activated wet resin was packed in a glass chromatography column with an inner diameter of 26 mm and a height of 400 mm, and the Citrulline extract solution after fermentation by microorganisms was passed through the resin column at a rate of 2 BV/h to adsorb Citrulline.

(3) Macroporous adsorption resin discoloration: mixed XAD-761 activated wet resin with Citrulline eluent at 1:20 (g/mL), and performed static adsorption on condition of 100-150 r/min for 2 hours at room temperature.

(4) Crystallization and recrystallization.

a. The crude Citrulline extract was concentrated under vacuum to a soluble solid with the content ≥30%, the pH of the concentrated solution was adjusted to 5.97, and the Citrulline crystals were precipitated at 4° C. The precipitate was centrifuged, washed, and dried to obtain a white powdered solid of Citrulline crystals.

b. Dissolved the Citrulline powder of step (a) with water, adjusted the pH to 5.97, added 0.1% Citrulline crystals as seed crystals, precipitated the Citrulline crystals at 4° C., and centrifuged to separate the precipitates.

c. Repeated step (b) 1-2 times, centrifuged the precipitate, washed, and dried to obtain a refined solid powder of Citrulline.

It is determined that the extraction rate of Citrulline in the above method was 93.43%, and the purity of the Citrulline extract after purification was 99.35%.

Embodiment 2

A method for extracting Citrulline from watermelon, the steps are as follows: the ratio of resin to Citrulline extract is 1:15 (g/mL).

1. Raw Material Pretreatment

After the outer skin of the watermelon rind is removed, the rind is squeezed and filtered to obtain filter residue or the rind which is dried is ground into a powder;

2. Ultrasound-Enzymatic Hydrolysis Assisted Solvent Leaching

Water was added to the pretreated material at a material-liquid ratio of 1:15 (kg/L), and then 0.1% (m/m) of pectinase and 0.1% (m/m) of cellulose were also added to the above pretreated material. Adjusted the pH of the enzymatic hydrolysis to 4.0, ultrasonic power to 120 W, extraction temperature to 30° C., extraction time to 60 min, and extraction times to twice to obtain an extract.

3. Purification (1) Microbial fermentation: 5% (v/v) yeast was added to the extract or mixed solution of the extract and melon peel juice to ferment for 24 hours to remove sugar.

(2) Ion-exchange resin purification: the liquid of Citrulline extract after microbial fermentation was filtered to remove yeasts, and added to HD-8 activated wet resin to perform the dynamic exchange adsorption of Citrulline, and then eluted with 0.5 mol/L ammonia solution to obtain Citrulline eluent; the elution rate is 2 BV/h.

The dynamic exchange adsorption is that 180 g of activated wet resin was packed in a glass chromatography column with an inner diameter of 26 mm and a height of 400 mm, and the Citrulline extract solution after fermentation by microorganisms was passed through the resin column at a rate of 2 BV/h to adsorb Citrulline.

(3) Macroporous adsorption resin discoloration: mixed XAD-761 activated wet resin with Citrulline eluent at 1:20 (g/mL), and performed static adsorption on condition of 100-150 r/min for 2 hours at room temperature.

(4) Crystallization and recrystallization.

a. The crude Citrulline extract was concentrated under vacuum to a soluble solid with the content ≥30%, the pH of the concentrated solution was adjusted to 5.97, and the Citrulline crystals were precipitated at 4° C. The precipitate was centrifuged, washed, and dried to obtain a white powdered solid of Citrulline crystals.

b. Dissolved the Citrulline powder of step (a) with water, adjusted the pH to 5.97, added 0.1% Citrulline crystals as seed crystals, precipitated the Citrulline crystals at 4° C., and centrifuged to separate the precipitates.

c. Repeated step (b) 1-2 times, centrifuged the precipitate, washed, and dried to obtain a refined solid powder of Citrulline.

It is determined that the extraction rate of Citrulline in the above method was 79.87%, and the purity of the Citrulline extract after purification was 97.65%.

Embodiment 3

A method for extracting Citrulline from watermelon, the steps are as follows:

1. Raw Material Pretreatment

After the outer skin of the watermelon rind is removed, the rind is squeezed and filtered to obtain filter residue or the rind which is dried is ground into a powder;

2. Ultrasound-Enzymatic Hydrolysis Assisted Solvent Leaching

Water was added to the pretreated material at a material-liquid ratio of 1:20 (kg/L), and then 0.1% (m/m) of pectinase and 0.1% (m/m) of cellulose were also added to the above pretreated material. Adjusted the pH of the enzymatic hydrolysis to 4.0, ultrasonic power to 140 W, extraction temperature to 40° C., extraction time to 120 min, and extraction times to twice to obtain an extract.

3. Purification (1) Microbial fermentation: 5% (v/v) yeast was added to the extract or mixed solution of the extract and melon peel juice to ferment for 24 hours to remove sugar.

(2) Ion-exchange resin purification: the liquid of Citrulline extract after microbial fermentation was filtered to remove yeasts, and added to HD-8 activated wet resin to perform the dynamic exchange adsorption of Citrulline, and then eluted with 0.5 mol/L ammonia solution to obtain Citrulline eluent; the elution rate is 2 BV/h;

The dynamic exchange adsorption is that 180 g of activated wet resin was packed in a glass chromatography column with an inner diameter of 26 mm and a height of 400 mm, and the Citrulline extract solution after fermentation by microorganisms was passed through the resin column at a rate of 2 BV/h to adsorb Citrulline.

(3) Macroporous adsorption resin discoloration: mixed XAD-761 activated wet resin with Citrulline eluent at 1:20 (g/mL), and performed static adsorption on condition of 100-150 r/min for 2 hours at room temperature.

(4) Crystallization and recrystallization.

a. The crude Citrulline extract was concentrated under vacuum to a soluble solid with the content ≥30%, the pH of the concentrated solution was adjusted to 5.97, and the Citrulline crystals were precipitated at 4° C. The precipitate was centrifuged, washed, and dried to obtain a white powdered solid of Citrulline crystals.

b. Dissolved the Citrulline powder of step (a) with water, adjusted the pH to 5.97, added 0.1% Citrulline crystals as seed crystals, precipitated the Citrulline crystals at 4° C., and centrifuged to separate the precipitates.

c. Repeated step (b) 1-2 times, centrifuged the precipitate, washed, and dried to obtain a refined solid powder of Citrulline.

It is determined that the extraction rate of Citrulline in the above method was 86.58%, and the purity of the Citrulline extract after purification was 98.11%.

COMPARATIVE EXAMPLE 1

A method for extracting Citrulline from watermelon, the steps are as follows:

1. Raw Material Pretreatment

After the outer skin of the watermelon rind is removed, the rind is squeezed and filtered to obtain filter residue or the rind which is dried is ground into a powder;

2. Ultrasound-Enzymatic Hydrolysis Assisted Solvent Leaching

Water was added to the pretreated material at a material-liquid ratio of 1:10 (kg/L), and then 0.1% (m/m) of pectinase and 0.1% (m/m) of cellulose were also added to the above pretreated material. Adjusted the pH of the enzymatic hydrolysis to 4.0, ultrasonic power to 100 W, extraction temperature to 50° C., extraction time to 90 min, and extraction times to twice to obtain an extract.

3. Purification (1) Microbial fermentation: 5% (v/v) yeast was added to the extract or mixed solution of the extract and melon peel juice to ferment for 24 hours to remove sugar.

(2) Ion-exchange resin purification: the Citrulline extract after microbial fermentation was filtered to remove yeasts, and added to HD-8 activated wet resin to perform the dynamic exchange adsorption of Citrulline, and then eluted with 0.1 mol/L ammonia solution for 2 BV/h of the elution rate.

The dynamic exchange adsorption is that 180 g of activated wet resin was packed in a glass chromatography column with an inner diameter of 26 mm and a height of 400 mm, and the Citrulline extract solution after fermentation by microorganisms was passed through the resin column at a rate of 2 BV/h to adsorb Citrulline.

(3) Macroporous adsorption resin discoloration: mixed XAD-761 activated wet resin with Citrulline eluent at 1:20 (g/mL), and performed static adsorption on condition of 100-150 r/min for 2 hours at room temperature.

(4) Crystallization and recrystallization.

a. The crude Citrulline extract was concentrated under vacuum to a soluble solid with the content of ≥30%, the pH of the concentrated solution was adjusted to 5.97, and the Citrulline crystals were precipitated at 4° C. The precipitate was centrifuged, washed, and dried to obtain a white powdered solid of Citrulline crystals.

b. Dissolved the Citrulline powder of step (a) with water, adjusted the pH to 5.97, added 0.1% Citrulline crystals as seed crystals, precipitated the Citrulline crystals at 4° C., and centrifuged to separate the precipitates.

c. Repeated step (b) 1-2 times, centrifuged the precipitate, washed, and dried to obtain a refined solid powder of Citrulline.

It is determined that the extraction rate of Citrulline in the above method was 74.28%, and the purity of the Citrulline extract after purification was 95.74%.

COMPARATIVE EXAMPLE 2

A method for extracting Citrulline from watermelon, the steps are as follows:

1. Raw Material Pretreatment

After the outer skin of the watermelon rind is removed, the rind is squeezed and filtered to obtain filter residue or the rind which is dried is ground into a powder;

2. Ultrasound-Enzymatic Hydrolysis Assisted Solvent Leaching

Water was added to the pretreated material at a material-liquid ratio of 1:10 (kg/L), and then 0.1% (m/m) of pectinase and 0.1% (m/m) of cellulose were also added to the above pretreated material. Adjusted the pH of the enzymatic hydrolysis to 4.0, ultrasonic power to 100 W, extraction temperature to 50° C., extraction time to 90 min, and extraction times to twice to obtain an extract.

3. Purification (1) Microbial fermentation: 8% (v/v) yeast was added to the extract or mixed solution of the extract and melon peel juice to ferment for 24 hours to remove sugar.

(2) Ion-exchange resin purification: the Citrulline extract after microbial fermentation was filtered to remove yeasts, and added to HD-8 activated wet resin to dynamically exchange and adsorb Citrulline, and then eluted with 1.0 mol/L ammonia solution for 2 BV/h of the elution rate.

The dynamic exchange adsorption is that 180 g of activated wet resin was packed in a glass chromatography column with an inner diameter of 26 mm and a height of 400 mm, and the Citrulline extract solution after fermentation by microorganisms was passed through the resin column at a rate of 2 BV/h to adsorb Citrulline.

(3) Macroporous adsorption resin discoloration: mixed XAD-761 activated wet resin with Citrulline eluent at 1:20 (g/mL), and performed static adsorption on condition of 100-150 r/min for 2 hours at room temperature.

(4) Crystallization and recrystallization.

a. The crude Citrulline extract was concentrated under vacuum to a soluble solid with the content of ≥30%, the pH of the concentrated solution was adjusted to 5.97, and the Citrulline crystals were precipitated at 4° C. The precipitate was centrifuged, washed, and dried to obtain a white powdered solid of Citrulline crystals.

b. Dissolved the Citrulline powder in step (a) with water, adjusted the pH to 5.97, added 0.1% Citrulline crystals as seed crystals, precipitated the Citrulline crystals at 4° C., and centrifuged to separate the precipitates.

c. Repeated step (b) 1-2 times, centrifuged the precipitate, washed, and dried to obtain a refined solid powder of Citrulline.

It is determined that the extraction rate of Citrulline in the above method was 79.73%, and the purity of the Citrulline extract after purification was 92.47%.

COMPARATIVE EXAMPLE 3

A method for extracting Citrulline from watermelon, the steps are as follows:

1. Raw Material Pretreatment

After the outer skin of the watermelon rind is removed, the rind is squeezed and filtered to obtain filter residue or the rind which is dried is ground into a powder;

2. Ultrasound-Enzymatic Hydrolysis Assisted Solvent Leaching

Water was added to the pretreated material at a material-liquid ratio of 1:10 (kg/L), and then 0.1% (m/m) of pectinase and 0.1% (m/m) of cellulose were also added to the above pretreated material. Adjusted the pH of the enzymatic hydrolysis to 4.0, ultrasonic power to 100 W, extraction temperature to 50° C., extraction time to 90 min, and extraction times to twice to obtain an extract.

3. Purification (1) Microbial fermentation: 3% (v/v) yeast was added to the extract or mixed solution of the extract and melon peel juice to ferment for 24 hours to remove sugar.

(2) Ion-exchange resin purification: the Citrulline extract after microbial fermentation was filtered to remove yeasts, and added to HD-8 activated wet resin to dynamically exchange and adsorb Citrulline, and then eluted with 0.5 mol/L ammonia solution for 1 BV/h of the elution rate.

The dynamic exchange adsorption is that 180 g of activated wet resin was packed in a glass chromatography column with an inner diameter of 26 mm and a height of 400 mm, and the Citrulline extract solution after fermentation by microorganisms was passed through the resin column at a rate of 4 BV/h to adsorb Citrulline.

(3) Macroporous adsorption resin discoloration: mixed XAD-761 activated wet resin with Citrulline eluent at 1:20 (g/mL), and performed static adsorption on condition of 100-150 r/min for 2 hours at room temperature.

(4) Crystallization and recrystallization.

a. The crude Citrulline extract was concentrated under vacuum to a soluble solid with the content of ≥30%, the pH of the concentrated solution was adjusted to 5.97, and the Citrulline crystals were precipitated at 4° C. The precipitate was centrifuged, washed, and dried to obtain a white powdered solid of Citrulline crystals.

b. Dissolved the Citrulline powder of step (a) with water, adjusted the pH to 5.97, added 0.1% Citrulline crystals as seed crystals, precipitated the Citrulline crystals at 4° C., and centrifuged to separate the precipitates.

c. Repeated step (b) 1-2 times, centrifuged the precipitate, washed, and dried to obtain a refined solid powder of Citrulline.

It is determined that the extraction rate of Citrulline in the above method was 84.77%, and the purity of the Citrulline extract after purification was 97.63%.

Effect of Different Temperature and Time on Citrulline Extraction

Based on the extraction method of Example 1, in the process of ultrasound-assisted solvent extraction, three different extraction temperatures such as 30, 40, and 50° C. were used, and different extraction times (30, 60, 90, 120, 180 min) were set at each extraction temperature to study the effect of different temperature and time on the effect of Citrulline extraction. The results are shown in FIG. 1.

It can be seen from FIG. 1 that increasing the temperature can accelerate the extraction of Citrulline, and also has a certain effect on improving the extraction rate. However, with the increase of temperature, the solubility of other ingredients in watermelon rind will increase, and the Maillard reaction will intensify, which will cause difficulties in subsequent purification work. Therefore, the extraction temperature should not exceed 50° C. At the same time, it can be seen from FIG. 1 that with the increase of extraction time, the amount of Citrulline extracted increase slightly, but it can be extracted completely after 1.5 hours, and further extension of the extraction time has little effect on the increase of extraction rate. Therefore, 1.5-2 hours is chosen as the better extraction time.

Effect of Different Methods on Citrulline Extraction

Based on the extraction method of Citrulline in Example 1, without ultrasound-assisted extraction (complex enzymatic method), without enzymatic hydrolysis (ultrasonic method), the solvent extraction method (control) with neither ultrasound-assisted extraction nor enzymatic hydrolysis and the extraction method (ultrasound-enzymatic method) of Example 1 were used to extract Citrulline in watermelon. The extraction effect was measured as shown in FIG. 2.

Figure 2:
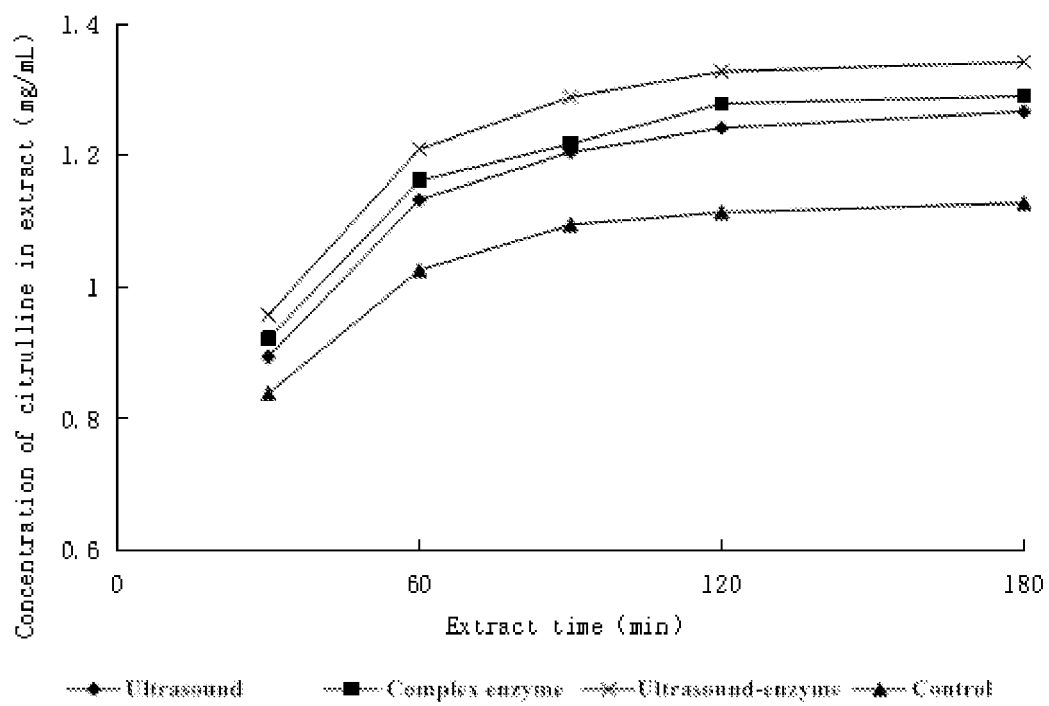
FIG. 2 shows the effect of different extraction methods on Citrulline extraction.

It can be seen from FIG. 2 that both the ultrasonic extraction and the complex enzymatic treatment can improve the extraction effect of Citrulline. In addition, the ultrasound-enzymatic method has the best extraction effect on Citrulline.

Effect of Different Enzyme Treatments on the Citrulline Extraction

Based on the Citrulline extraction method in Example 1, different biological enzymes were added to perform enzymolysis treatment on rind with outer skin was removed, and the effect of different enzyme treatments on the Citrulline extraction was measured. The results are shown in Table 1.

TABLE 1

Effect of different enzyme treatments on Citrulline extraction in watermelon rind

| Treatment | Addition | Concentration of Citrulline in extract (mg/mL) |
|---|---|---|
| Pectinase | 0.2% | 1.227 |
| Cellulase | 0.2% | 1.205 |
| Pectinase + Cellulase | 0.1% + 0.1% | 1.278 |
| Control (not processed) | — | 1.114 |

The results in Table 1 show that the addition of pectinase and cellulase towards raw materials of watermelon rind to perform pretreatment is beneficial to the extraction of Citrulline, and the effect of the combined enzyme treatment is better than that of any single enzyme treatment.

Effect of the Number of Extractions on Citrulline Extraction

Based on the Citrulline extraction method of Example 1, the amount of Citrulline was detected for each extraction, and the total extraction was performed 3 times. The results are shown in Table 2:

TABLE 2

Effect of extraction times on extraction rate

| | Number of extractions | | |
|---|---|---|---|
| | 1 | 2 | 3 |
| Concentration of Citrulline in extract (mg/mL) | 1.412 | 0.410 | 0.089 |
| Extraction rate (%) | 72.41 | 21.02 | 4.72 |

As can be seen from Table 2, the method of the present invention can efficiently extract Citrulline from watermelon rind. After three extractions, more than 98% of Citrulline can be extracted from watermelon rind. Among them, the first two extraction rates reach 93.43%. So in the extraction of Citrulline from watermelon rind, it is sufficient to extract twice.

Effect of Microbial Fermentation on Citrulline Content

5% (v/v) yeast was added to the crude Citrulline extract to ferment for 24 hours. The changes in sugar and Citrulline content before and after fermentation were compared. The results are shown in Table 3.

TABLE 3

Comparison of sugar and Citrulline content before and after fermentation

| Test items | Before fermentation | After fermentation |
|---|---|---|
| Total sugar (mg/mL) | 12.90 | 2.31 |
| Citrulline concentration (mg/mL) | 1.56 | 1.52 |

As can be seen from Table 3, after the crude Citrulline extract is fermented by yeast, the total sugar content decreases sharply, but the Citrulline content changes little, indicating that the microbial fermentation method can effectively remove the sugar in it, and has little effect on the Citrulline content.

Effect of Different Ion-Exchange Resins on the Adsorption of Citrulline (1) Static Adsorption Took 5 g each of five types of activated wet resins, put them in 250 mL stoppered conical flasks, and added 100 mL of crude Citrulline extract to perform static adsorption on a shaker at room temperature. Determined the content of residual Citrulline of extraction after 8 hours, and then investigated the adsorption effect of different resins on Citrulline. The results are shown in Table 4.

TABLE 4

Adsorption effect of Citrulline by different resins

| | Resin model | | | | |
|---|---|---|---|---|---|
| | D001 | D113 | HD-8 | 732 | 252H |
| Content of Citrulline in the original extract (mg/mL) | 5.26 | 5.26 | 5.26 | 5.26 | 5.26 |
| Citrulline content after | 4.20 | 4.79 | 3.43 | 3.83 | 4.33 |

TABLE 4-continued

Adsorption effect of Citrulline by different resins

| | Resin model | | | | |
|---|---|---|---|---|---|
| | D001 | D113 | HD-8 | 732 | 252H |
| adsorption (mg/mL) | | | | | |
| Equilibrium adsorption capacity (mg/g wet resin) | 21.18 | 9.33 | 36.69 | 28.55 | 18.49 |
| Adsorption percentage (%) | 20.13 | 8.87 | 34.88 | 27.14 | 17.58 |

As the results in Table 4, it is known that the selected cationic resins can exchange and adsorb Citrulline in the crude Citrulline extract. Among them, strong acid ion-exchange resins such as D001, HD-8, 732, and 252H have a stronger exchange adsorption capacity, while D113 is a weak acid ion exchange resin, which has a weaker exchange adsorption capacity for Citrulline. In addition, among the four strong acid ion exchange resins, HD-8 resin has the strongest exchange capacity for Citrulline in the crude Citrulline extract, and its equilibrium adsorption capacity reaches 36.69 mg/g wet resin.

(2) Effect of Adsorption Time on HD-8 Resin Exchanging Citrulline

Took 10 g of activated HD-8 wet resin, put it in a 250 mL stoppered conical flask, and added 150 mL of crude Citrulline extract to perform static adsorption in a shaker under normal temperature conditions, and periodically sampled to determine the remaining concentration of Citrulline in the supernatant to investigate the dynamic equilibrium time of HD-8 resin exchange adsorption of Citrulline. The results are shown in FIG. 3.

Figure 3:
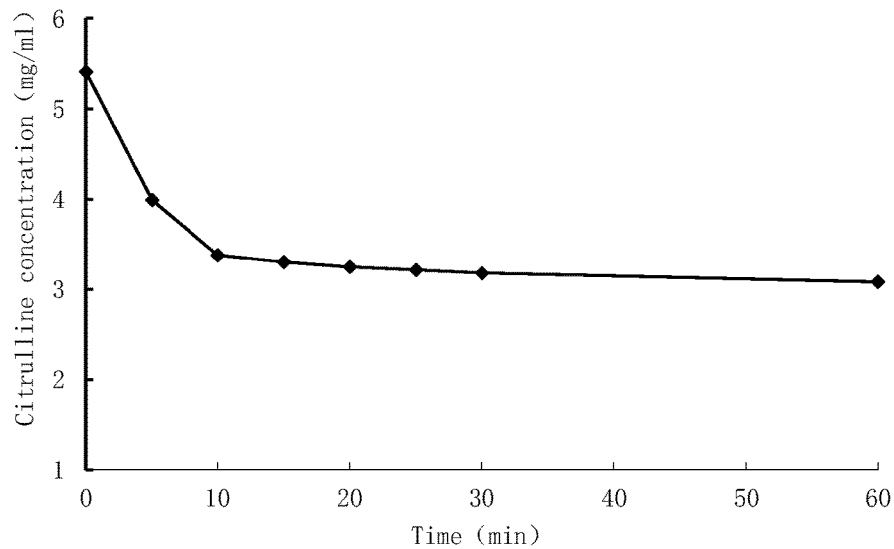
FIG. 3 shows the effect of adsorption time on HD-8 resin exchange adsorption of Citrulline.

It can be seen from FIG. 3 that the rate of exchanging and adsorbing Citrulline by HD-8 resin is very fast, and the Citrulline in the adsorption extract is quickly exchanged within the first 5 minutes. The rate becomes slowly after 5 minutes, and then reaches equilibrium after 15 minutes.

(3) Dynamic Exchange Adsorption 180 g of activated wet resin was packed in a glass chromatography column with an inner diameter of 26 mm and a height of 400 mm, and the crude Citrulline extract was passed through the resin column at room speeds of 2, 4, and 6 BV/h respectively. The residual Citrulline content in the effluent was collected and measured to investigate the dynamic exchange adsorption effect of HD-8 resin on Citrulline. The results are shown in FIG. 4.

Figure 4:
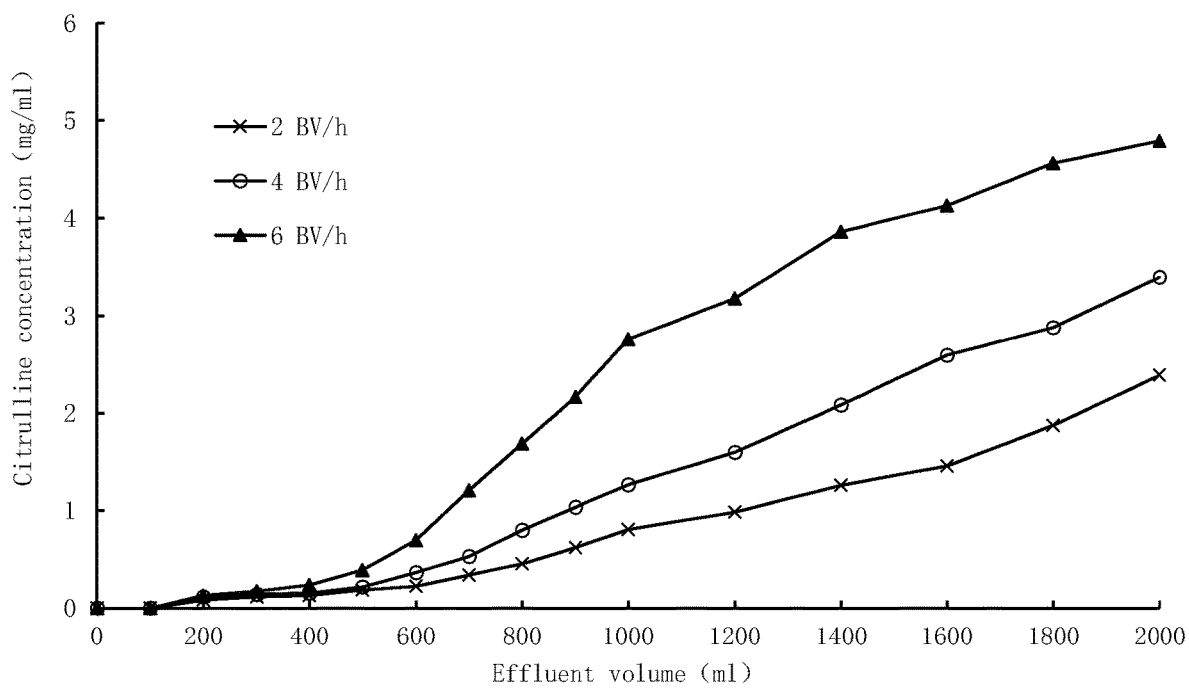
FIG. 4 shows the dynamic exchange adsorption curve of Citrulline with HD-8 resin.

It can be seen from FIG. 4 that with the increase of the volume of the effluent, the concentration of residual Citrulline in the column solution also gradually increases, indicating that the adsorption percentage of Citrulline in the extract by the HD-8 resin gradually decreases. In addition, as the flow velocity of the column is reduced, the leakage rate of Citrulline is also greatly reduced, and the rate of decrease of the adsorption percentage is significantly slower, indicating that appropriately reducing the flow rate of the column can increase the dynamic adsorption effect. This is because when the flow velocity through the column is too large, the Citrulline in the extraction solution has no time to diffuse to the inner surface of the resin, which causes the HD-8 resin to rapidly decrease the adsorption percentage of Citrulline in the extraction solution. Therefore, a flow rate of 2 BV/h is more appropriate. At this flow rate, when the effluent volume is 2000 mL, the adsorption percentage can still reach more than 50%.

Decoloration Effect of Citrulline Eluent with Different Macroporous Adsorption Resins Weighed 5 g of XDA-5, XAD-761, AB-8, HZ-803 activated wet resin into 250 mL stoppered triangle flasks respectively, and added 100 mL Citrulline eluent to perform static adsorption on the condition of 100-150 r/min at room temperature. After 2 hours, the light transmittance and Citrulline concentration were measured after filtration and sampling to investigate the effect of different macroporous adsorption resins on the removal of pigment from the Citrulline eluate under static adsorption conditions. The results are shown in the Table 5.

TABLE 5

Decolorization effect of Citrulline eluent with different macroporous adsorption resins

| | Light transmittance | | Citrulline concentration (mg/mL) | |
|---|---|---|---|---|
| Resin model | Before adsorption | After adsorption | Before adsorption | After adsorption |
| XDA-5 | 78.2 | 97.4 | 7.26 | 7.15 |
| XAD-761 | 78.2 | 98.2 | 7.26 | 7.22 |
| AB-8 | 78.2 | 98.7 | 7.26 | 7.06 |
| HZ-803 | 78.2 | 97.9 | 7.26 | 7.18 |

It can be known from Table 5 that the four macroporous adsorption resins tested can effectively remove the pigment in the Citrulline eluent, and the adsorption of Citrulline is less. Considering the decolorization effect and the adsorption of Citrulline, it is better to use XAD-761 macroporous adsorption resin to decolor the Citrulline eluent.

Analysis Results of Citrulline Extract of the Present Invention

The physicochemical properties and hygienic indicators of the Citrulline extract extracted in Example 1 were analyzed and compared with the quality standards of commercially available Citrulline products. The results are shown in Table 6.

TABLE 6

Physicochemical properties and hygienic indicators of Citrulline extract

| Test item | Unit | Test result | Commercial product standard |
|---|---|---|---|
| Citrulline content | % | 92.48 | — |
| Ammonium content ($NH_4$) | % | <0.02 | ≤0.02 |
| Chloride | % | <0.02 | ≤0.02 |
| Sulfate ($SO_4$) | % | <0.02 | ≤0.02 |
| Iron | mg/kg | <10 | ≤10 |
| Arsenic | mg/kg | $2.7 \times 10^{-2}$ | ≤1 |
| Lead | mg/kg | Not detected | ≤10 |

From the test results in Table 6, it can be known that the heavy metal and microbe indexes of the Citrulline extract extracted by the method of the present invention meet the relevant sanitary requirements and product quality standards.

The above embodiments are only used to illustrate the technical solutions of the present invention, but not to limit them. Although the present invention has been described in detail with reference to the foregoing embodiments, the technical solutions described in the embodiments are still possibly modified, or some of the technical features are equivalently replaced by those skilled in the art by referring to the foregoing. These modifications or replacements do not depart from the spirit and scope of the technical solutions claimed in the present invention.

What is claimed is:

1. A method for extracting Citrulline from watermelon, comprising the steps of pretreating the watermelon, ultrasound-enzymatic hydrolysis assisted solvent leaching and purification;

the step of purification includes:
(1) microbial fermentation: adding 5% (v/v) yeast to a Citrulline extract and conducting a fermentation for 24 hours to remove the amount of sugar in the Citrulline extract;
(2) ion-exchange resin purification: filtering the Citrulline extract to remove the yeast, passing the Citrulline extract over an HD-8 activated wet resin to adsorb the Citrulline, and eluting the HD-8 activated wet resin with 0.5 mol/L ammonia solution at an elution rate of 2 BV/h to obtain a Citrulline eluent;
(3) macroporous adsorption resin discoloration: mixing a XAD-761 activated wet resin with the Citrulline eluent at a ratio of 1:20 (g/mL), and performing a static adsorption at 100-150 r/min for 2 hours at room temperature to obtain a crude Citrulline extract;
(4) crystallization and recrystallization:
   a. concentrating the crude Citrulline extract under vacuum to obtain a concentrated solution with a soluble solid content ≥30%, adjusting the pH of the concentrated solution to 5.97, and precipitating at 4° C., centrifuging, washing and drying to obtain a white powdered solid of Citrulline crystals,
   b. dissolving the white powered solid of step (a) with water, adjusting the pH to 5.97, adding 0.1% Citrulline crystals as seed crystals, precipitating at 4° C., and centrifuging to obtain a precipitate,
   c. recrystallizing the precipitate from step (4)b by dissolving the precipitate with water, adjusting the pH to 5.97, adding 0.1% Citrulline seed crystal, precipitating and centrifuging to obtain a refined solid powder of Citrulline.

2. The method for extracting Citrulline from watermelon according to claim 1, wherein the step of the ultrasound-enzymatic hydrolysis assisted solvent leaching includes adding 0.1-0.2% biological enzyme to the pretreated watermelon.

3. The method for extracting Citrulline from watermelon according to claim 2, wherein the biological enzyme is pectinase, cellulase, or a combination thereof.

4. The method for extracting Citrulline from watermelon according to claim 1, wherein the ultrasonic-enzymatic hydrolysis assisted solvent leaching is conducted twice at a material-liquid ratio of 1:10-1:20 (kg/L), an ultrasonic power of 100-140 W, an extraction temperature of 30-50° C., and an extraction time of 60-120 min.

5. The method for extracting Citrulline from watermelon according to claim 1, wherein:
pretreating the watermelon includes:
   removing an outer skin of the watermelon to obtain a watermelon rind, squeezing the watermelon rind and filtering to obtain a filtered residue or grounding the watermelon rind into a powder;
ultrasound-enzymatic hydrolysis assisted solvent leaching includes:
   adding water to the filtered residue or the powder at a material-liquid ratio of 1:10-1:20 (kg/L) to form a mixture, and then adding 0.1% (w/w) of pectinase and 0.1% (w/w) of cellulose to the mixture; adjust pH to 4.0, sonicating the mixture twice at an ultrasonic power of 100-140 W, at an extraction temperature of 30-50° C., for 60-120 min to obtain the Citrulline extract.

6. The purification method of Citrulline according to claim 1, wherein the ion-exchange resin purification is a shaker static adsorption or a dynamic exchange adsorption.

7. The purification method of Citrulline according to claim 6, wherein:
the shaker static adsorption includes mixing the HD-8 activated wet resin and the Citrulline extract in a ratio of 1:15-20 (g/mL), and then performing a static adsorption at 100-150 r/min for 15 min; and
the dynamic exchange adsorption includes packing 180 g of HD-8 activated wet resin in a glass chromatography column with an inner diameter of 26 mm and a height of 400 mm, and passing the Citrulline extract through the glass chromatography column at a speed of 2-6 BV/h to adsorb the Citrulline.

* * * * *